United States Patent
Van Berkel et al.

(10) Patent No.: US 9,140,633 B2
(45) Date of Patent: Sep. 22, 2015

(54) ENHANCED SPOT PREPARATION FOR LIQUID EXTRACTIVE SAMPLING AND ANALYSIS

(75) Inventors: Gary J. Van Berkel, Oak Ridge, TN (US); Richard C. King, Quakertown, PA (US)

(73) Assignee: UT-Battelle, LLC, Oak Ridge, TN (US)

( * ) Notice: Subject to any disclaimer, the term of this patent is extended or adjusted under 35 U.S.C. 154(b) by 363 days.

(21) Appl. No.: 13/488,141

(22) Filed: Jun. 4, 2012

(65) Prior Publication Data
US 2012/0304747 A1     Dec. 6, 2012

Related U.S. Application Data

(60) Provisional application No. 61/493,068, filed on Jun. 3, 2011.

(51) Int. Cl.
*G01N 1/38* (2006.01)
*H01J 49/04* (2006.01)

(52) U.S. Cl.
CPC ............ *G01N 1/38* (2013.01); *G01N 2001/383* (2013.01); *H01J 49/0404* (2013.01); *H01J 49/0468* (2013.01)

(58) Field of Classification Search
CPC ....................................................... G01N 1/38
USPC ...................................................... 73/61.59
See application file for complete search history.

(56) References Cited

U.S. PATENT DOCUMENTS

| | | | |
|---|---|---|---|
| 5,898,005 A | 4/1999 | Singh et al. | |
| 6,210,978 B1 | 4/2001 | Hatch et al. | |
| 6,803,566 B2 * | 10/2004 | Van Berkel | 250/288 |
| 7,122,790 B2 * | 10/2006 | Fonash et al. | 250/288 |
| 7,295,026 B2 | 11/2007 | Van Berkel et al. | |
| 2002/0187312 A1 * | 12/2002 | Fonash et al. | 428/195 |
| 2003/0193020 A1 * | 10/2003 | Van Berkel | 250/288 |
| 2004/0161860 A1 | 8/2004 | Richalet-Secordel et al. | |
| 2009/0227466 A1 | 9/2009 | Kim et al. | |
| 2010/0002905 A1 | 1/2010 | Van Berkel et al. | |
| 2010/0224013 A1 * | 9/2010 | Van Berkel et al. | 73/863.81 |
| 2011/0053794 A1 | 3/2011 | Zhang | |

OTHER PUBLICATIONS

Dhirendra, K.; Lewis, S.; Udpa, N.; Atin, K. "Solid Dispersions: A review"; Pak. J. Pharm. Sci., 2009, 22, 234-246.

Sigma-Aldrich, Analytix Advances in Analytical Chemistry, vol. 6 (2001) 1-6.

ElNaggar, Barbier, VanBerkel, "Liquid Microjunction Surface Sampling Probe Fluid Dynamics: Computational and Experimental Analysis of Coaxial Intercapillary Positioning Effects on Sample Manipulation" J. Am Soc. Mass Spectrum (2011) 22:1157-1166.

(Continued)

*Primary Examiner* — Peter Macchiarolo
*Assistant Examiner* — Nathaniel Kolb
(74) *Attorney, Agent, or Firm* — Novak Druce Conolly Bove + Quigg LLP

(57) ABSTRACT

A method for performing surface sampling of an analyte, includes the step of placing the analyte on a stage with a material in molar excess to the analyte, such that analyte-analyte interactions are prevented and the analyte can be solubilized for further analysis. The material can be a matrix material that is mixed with the analyte. The material can be provided on a sample support. The analyte can then be contacted with a solvent to extract the analyte for further processing, such as by electrospray mass spectrometry.

7 Claims, 3 Drawing Sheets

(56) References Cited

OTHER PUBLICATIONS

Van Berkel, Kertesz, "High-Throughput Mode Liquid Microjunction Surface Sampling Probe" Anal. Chem. (2009) 81, 7096-7101.

Kertesz, Van Berkel, "Fully automated liquid extraction-based surface sampling and ionization using a chip-based robotic nanoelectrospray platform" J. Mass. Spectrom (2010) 45, 252-260.
International Search Report mailed Aug. 21, 2012 PCT/US2012/40757.

* cited by examiner

ENHANCED SPOT PREPARATION FOR LIQUID EXTRACTIVE SAMPLING AND ANALYSIS

CROSS-REFERENCES TO RELATED APPLICATIONS

This application claims benefit under 35 U.S.C. §119(e) to U.S. Provisional Patent Application Ser. No. 61/493,068 filed on Jun. 3, 2011, which is hereby incorporated by reference in its entirety.

STATEMENT REGARDING FEDERALLY SPONSORED RESEARCH

This invention was made with government support under Contract No. DE-AC05-00OR22725 awarded by the U.S. Department of Energy. The government has certain rights in this invention.

FIELD OF THE INVENTION

This invention relates generally to surface sampling and analysis, and more particularly to surface sampling of analytes, which are not readily soluble in solvents used for such analysis.

BACKGROUND OF THE INVENTION

Currently available laser desorption techniques allow analysis of the chemical composition of surfaces at the micron level. However, conventional laser desorption techniques can be limited in their ability to desorb and ionize analytes present at the surface being analyzed. For example, preparation of dried sample spots on planar media is becoming a popular sample storage, preparation, shipping and analysis medium. In liquid extractive sampling of such prepared spots, fast, reproducible, and efficient reconstitution of the desired analyte is required to make direct analysis analytically viable. In such samples, the analyte of interest can sometimes crystallize, agglomerate, or take other intractable forms which are difficult to solubilize. Therefore, a need exists for improved surface extraction technology.

MALDI (matrix-assisted laser desorption/ionization) is a laser-based soft ionization method that has proven to be an effective ionization method for mass spectrometric analysis and investigation of large molecules. This method was developed in the late 1980s from such other desorption/ionization mass spectrometric methods as FAB (fast atom bombardment) and LDIMS (laser desorption ionization mass spectrometry). MALDI facilitates the production of intact gas-phase ions from large, nonvolatile, and thermally labile compounds such as proteins, oligonucleotides, synthetic polymers and large inorganic compounds by embedding these compounds in a chemical matrix. A laser beam (UV- or IR-pulsed laser) serves as the desorption and ionization source. The matrix absorbs the laser light energy and causes a small part of the target substrate to vaporize. The vaporized and ionized molecules are transferred electrostatically into a mass spectrometer where they are separated from the matrix ions and individually detected, usually by TOF (time-of-flight) mass spectrometry. The MALDI matrix must embed and isolate analytes, be soluble in solvents compatible with the analyte of interest, be vacuum stable, absorb the laser wavelength, cause co-desorption of the analyte upon laser irradiation, and promote analyte ionization.

A number of variations of the MALDI method are known. These include dried droplet, vacuum-drying crystallization, crushed-crystal, fast-evaporation, overlayer, sandwich, spin-coating, electrospray, quick & dirty (Q&D), matrix-pre-coated layers, chemical liquid, particle-doped (two-phase) liquid, chemical-doped liquid, solid supports, and MALDI on 2D-gels. In the case of samples that are insoluble it has been found that by pressing a mixture of finely ground sample and analyte, it is possible to record MALDI data from such compounds.

Electrospray is an alternative to MALDI. Electrospray generally involves flowing a sample liquid into an electrospray ion source comprising a small tube or capillary which is maintained at a high voltage, in absolute value terms, with respect to a nearby surface. The nearby (e.g. 1 cm) surface is commonly referred to as the counter electrode. Conventional ES systems for mass spectrometry apply high voltage (relative to a ground reference) to the emitter electrode while holding the counter electrode at a lower, near ground reference voltage. For the positive ion mode of operation, the voltage on the emitter is high positive, while for negative ion mode the emitter voltage is high negative. Liquid introduced into the tube or capillary is dispersed and emitted as fine electrically charged droplets (plume) by the applied electrical field.

The ionization mechanism generally involves the desorption at atmospheric pressure of ions from the fine electrically charged particles. The ions created by the electrospray process can then be used for a variety of applications, such as mass analyzed in a mass spectrometer.

In a typical ES-MS process, a solution containing analytes of interest is directed to the ES emitter which is held at high voltage, resulting in a charged solvent droplet spray or plume. The droplets drift towards the counter electrode under the influence of the electric field. As the droplets travel, gas-phase ions are liberated from the droplets. This process produces a quasi-continuous steady-state current with the charged droplets and ions constituting the current and completing the series circuit. A particularly useful application for electrospray is the production of gas phase ions from analytes in liquid solutions delivered by methods such as high pressure liquid chromatography, capillary electrophoresis or capillary electrochromatography to a system for detection and analysis, such as a mass spectrometer (MS).

Although ES MS has been known, the use of ES-MS for automatically reading out a plurality of spots, has been more recently developed. This is likely because of the technical challenges of sampling analytes from small spots on a sample surface with a liquid flow system in an automated way. Specifically, electrospray normally operates by having a sample dissolved in solution flow through transfer tubing to the ion source of the mass spectrometer. When trying to analyze a surface with electrospray, a significant challenge is presented in producing a probe suitable for transporting a normally solid-state surface sample into solution and then into the transfer line. In addition, a sophisticated structure is needed to control the alignment of the probe with the surface, the structure generally providing fine resolution of the probe movement relative to the surface.

Several methods for conducting surface sampling for electrospray mass spectrometry analysis, as well as other kinds of analysis, have been developed. Some such systems and methods are shown in US patents and Publications Nos. U.S. Pat. No. 6,803,566; U.S. Pat. No. 7,295,026, US 2010/0002905, and US 2010/0224013. The disclosure of these patents and publications is hereby incorporated fully by reference.

Once a way to sample the surface has been achieved, the next challenge is to dissolve the target sample analytes from the surface of interest. In liquid extractive sampling of such prepared spots, fast, reproducible, and efficient reconstitution of the desired analyte is required to make direct analysis analytically viable. In such samples, the analyte of interest can sometimes crystallize, agglomerate, or take other intractable forms which are difficult to solubilize. Therefore, a need exists for improved surface extraction technology.

SUMMARY OF THE INVENTION

The invention provides for the preparation of an analyte of interest by incorporating a matrix material with the analyte, or by depositing the analyte on a surface, which will prevent analyte-analyte interactions or interactions with other materials such that the analyte will not take an intractable form and can be dissolved for processing by surface sampling techniques. The surface sampling techniques can include but are not limited to various electrospraying techniques, atmospheric pressure chemical ionization (APCI), atmospheric pressure photoionization (APPI). Indeed, the sampling probes can be connected to any liquid introduction ionization source.

BRIEF DESCRIPTION OF THE DRAWINGS

A fuller understanding of the present invention and the features and benefits thereof will be obtained upon review of the following detailed description together with the accompanying drawings, in which.

DETAILED DESCRIPTION OF THE INVENTION

Figure 1A:
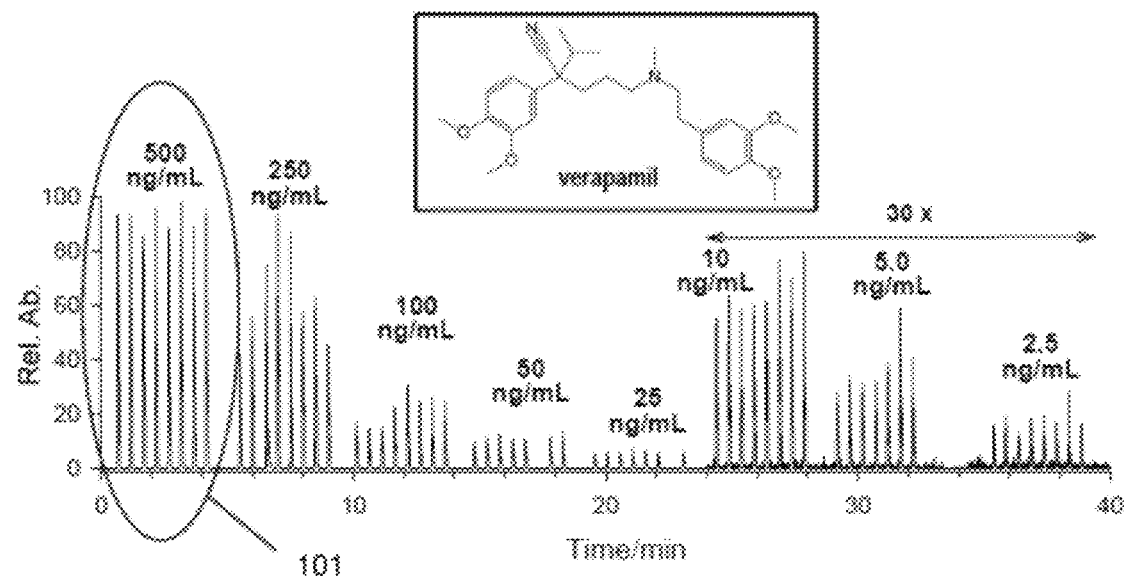
FIG. 1A is a Selected Reaction Monitoring (SRM) ion current chronogram obtained from the sampling of 64 different spots (1 µL deposited) of the analyte verapamil (500-2.5 ng/mL, 8 replicates for each concentration) and propranolol internal standard (100 ng/mL) from a stainless steel MALDI plate insert.

The invention provides for enhanced surface sampling of compounds which are prone to take intractable forms and are difficult to solubilize and process by known surface sampling techniques. This is accomplished by combining the specimen of interest with one or more matrix materials in molar excess to the analyte of interest. The presence of the matrix materials interferes with analyte-analyte or interactions with other materials, and thus prevents the analyte from crystallizing, agglomerating, or otherwise taking an intractable form. The analyte and matrix material can then be processed by known surface sampling techniques. A preferred surface sampling technique is electrospray surface sampling. Various types of spot sampling can also be employed, such as are described in Kertesz et al., Fully automated liquid extraction-based surface sampling and ionization using a chip-based robotic nanoelectrospray platform, J. Mass. Spectrom, 2010, 45, 25-260 (2009), which is hereby incorporated by reference in its entirety.

The term "molar excess" as used herein means that the matrix materials be sufficiently in molar excess to the analyte of interest that substantial analyte-analyte interactions or interactions with other materials do not occur. Such excess can be a 10× excess, or 50×, 100×, 500×, 1000×, 5000×, 10000×, 15000×, or 20000× molar excess. At the upper limit, the excess of the matrix material must not be so great as to dilute the analyte of interest to the point that meaningful analytical results cannot be attained. At the lower limit, the matrix material must be sufficiently in excess that substantial analyte-analyte interactions or interactions with other materials are not possible such as would result in the analyte taking an intractable form.

The term "intractable form" as used herein means a physical being of a material that prevents or precludes the material reaching a fluid state or becoming part of a liquid solution. Intractable forms of a material may include pure crystals, polymerized material, mixed solids and/or reaction products.

It is also possible to prevent such analyte-analyte interactions by placing the analyte on a specimen support that contains a material that will prevent such interactions. The material can be part of the surface material, or can be another material that is applied to the sample support. In either case, the surface will have particular chemical and physical characteristics that can be used to provide samples with the desired reconstitution properties.

The invention can have utility when used with different samples. These can include, without limitation, arrays, tissue, tablets, plates and wells. Examples of suitable analytes that can be used, sampled, and analyzed using the methods and materials of the invention include organic materials such as polymers, biological materials such as blood, tissue, skin, CSF, plasma, serum, saliva, tears, sweat, gastric fluid, synovial fluid, mucus, breath, sperm, vaginal fluid, bacteria, viruses, embryos, cells, organs, organ slices, organelles, fruit, leaves, vegetables; biological molecules such as proteins, peptides, nucleic acids, amino acids, drugs, natural products, metabolites, DNA, RNA, polypeptides, polynucleotides, polysaccharides, simple sugars, hormones, antibodies, carbohydrates, fatty acids, lipids; and inorganic materials and mixtures like fullerenes, pigments, coatings, paints, capsules, food and drug packaging, tablets and surfaces like glass, stainless steel, aluminum, copper, zinc, silver, gold, platinum, carbon, plastic, carpet, wall covering, paneling, milk containers, soda containers, cloth, clothing, paper, tape, photographic film, wax, cardboard, rubber, and oil.

Preparation of dried sample spots should maintain all current advantages of samples prepared as dried spots. These include low volumes, sample stability, and ease of storage and shipment. The chemical matrices, additives, or surfaces that provide these reconstitution properties must not contribute undue complications in the subsequent chemical analysis of the reconstituted sample. If mass spectrometry is the analysis method it is preferred that gas phase ion signals from the chemical materials or surfaces used would be minimal and not contribute to ionization suppression of the analyte or contribute ionic signals that are potentially isobaric with the analyte of interest.

The enhanced sample spot preparation will provide molecular dispersion of the analyte within the matrix/surface in a manner that prevents analyte agglomeration, self-crystallization or other chemical or physical associations that would prevent the rapid dissolution/reconstitution into solution by the solvents required for the analysis at hand.

A source of materials and sample preparation schemes to provide these characteristics can be found from existing literature on matrices used for matrix associated laser/desorption ionization (MALDI) and in literature related to topics like solid dispersions and co-crystallization.

For example, Van Berkel, Kertesz, King., Anal. Chem. 2009, 81, 7096-7101; (http://www.sigmaaldrich.com/etc/medialib/docs/Fluka/General_Information/fl_analytix6_2001_new.Par.0001.File.tmp/fl_analytix6_2001_new.pdf) describes source of materials and sample preparation schemes and is hereby incorporated by reference in its entirety. Similarly, Dhirendra, K.; Lewis, S.; Udpa, N.; Atin, K. "Solid Dispersions: A review"; Pak. J. Pharm. Sci., 2009, 22, 234-246, describes various preparation techniques for solid dispersions and is hereby incorporated by reference in its entirety.

Unlike MALDI, when using liquid extraction the chemical matrices no longer are required to have the proper properties for laser wavelength absorption or gas phase ion molecule chemistry for analyte ionization.

Different methods and materials are possible to produce the enhanced spot preparations of the invention. It will be understood that those included herein are for illustration purposes only, and the inclusion or omission of some or others is not intended to limit the scope or content of the invention.

Molecular Dispersion for Liquid Surface Sampling

Molecular dispersion is the isolation of molecules of less abundant substance within or at the surface of a molecular structure of a more abundant substance. Molecular dispersion describes liquids, solids, and gases. The more abundant component, the matrix, prevents the less abundant component from separating or crystallizing or otherwise creating particles whose main composition is the less abundant component.

The use of a molecular dispersion for creating a solid sample which rapidly re-dissolves can include fast dissolving materials, which are used in drug formulation, chemical formulation, fertilizer formulation, and cleaning products. Various embodiments of the invention provide for the incorporation of material for chemical analysis (analyte) in a molecular dispersion for the purpose of rapid re-dissolution of the dried sample for analysis of the analyte.

According to other embodiments, such a methodology can be enhanced when combined with surface sampling by a liquid microjunction surface sampling probe.

Figure 2A:
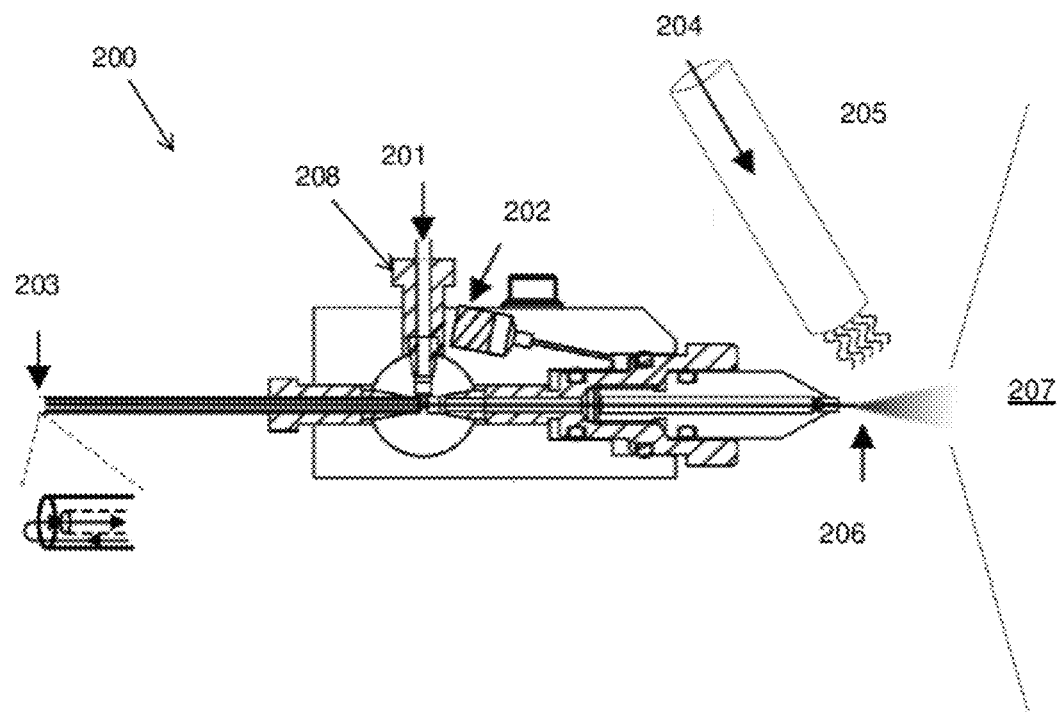
FIG. 2A is a schematic illustration of a liquid microjunction surface sampling probe.

Referring to FIG. 2A, a liquid microjunction surface sampling probe 200 is illustrated. The probe 200 includes an injection port 208 for receiving an eluting solvent 201, which flows from the injection port 208 to a sampling end 203.

Figure 2B:
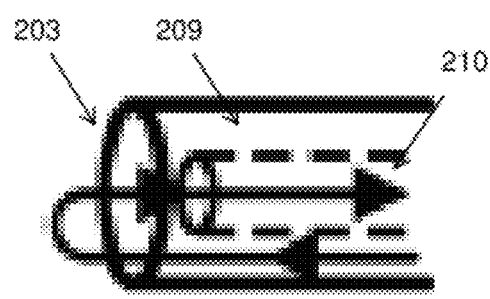
FIG. 2B is a schematic illustration of a sampling end of the liquid microjunction surface sampling probe illustrated in FIG. 2A.
Figure 3:
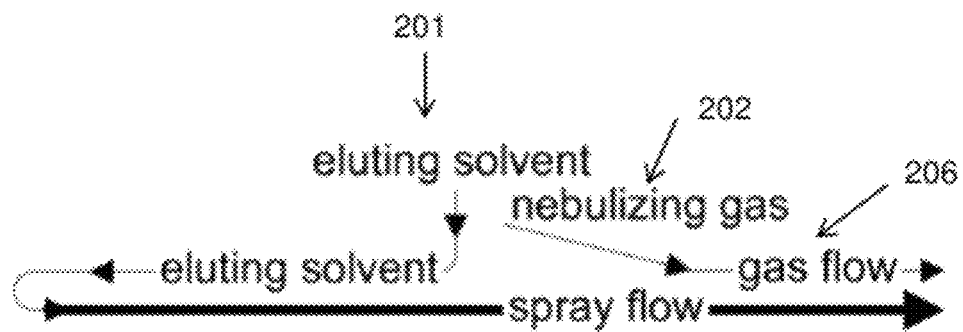
FIG. 3 is a flow diagram illustrating mass flow through the liquid microjunction surface sampling probe illustrated in FIG. 2A.
Figure 4:
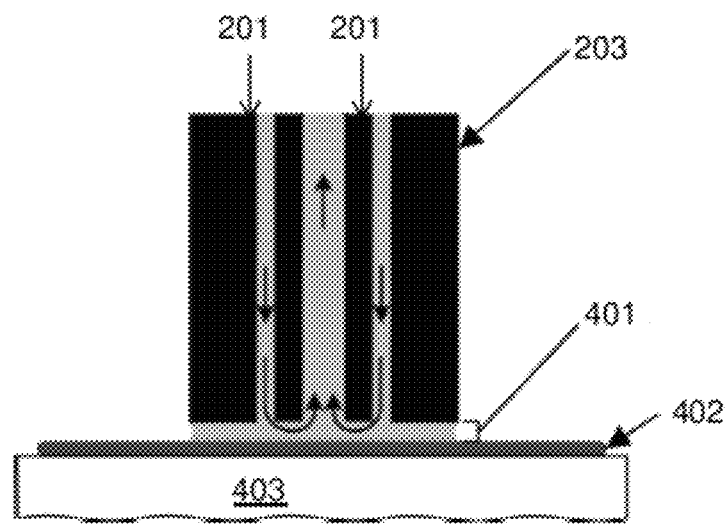
FIG. 4 is a schematic cross section of the sampling end of the liquid microjunction surface sampling probe illustrated in FIG. 2A.

Referring to FIG. 2B, the sampling end has an outer shaft 209 and an inner shaft 210. The eluting solvent 201 flows first through an annular opening between the outer shaft 209 and the inner shaft 210. As illustrated in FIG. 4, after exiting the annular opening between the outer shaft 209 and the inner shaft 210, the eluting solvent 201 arrives a liquid microjunction 401, where it contacts a sample spot 402 on a sample plate 403. After contacting the sample spot 402, the eluting solvent 201 is redirected through the inner shaft 210.

Referring again to FIG. 2A, nebulizing gas 202, such as Nitrogen (N2) is injected into the probe 200 and the eluting solvent 201 is emitted as a spray 206, where it can be heated via a heater 205, supplied with Nitrogen gas 204, before arriving at a nanospray atmospheric pressure interface 207.

The molecular dispersion must be capable of dissolution to result in a liquid sample with properties necessary to yield an analytically useful signal. The solution can for example support the formation of ions for mass spectrometry, can have the appropriate spectroscopic properties to allow detection of analyte by absorption or emission of light, can have the appropriate electrochemical properties to allow for electrochemical detection of the analyte in the solution containing the matrix, or the matrix compound can have the property of being separable from the analyte by other common analytical techniques.

According to various embodiments of the present invention, a molecular dispersion can be achieved through a variety of structures, including, but not limited to a dissolved chemical matrix, a biological matrix, a frozen liquid matrix, a polymer matrix, a sol gel/gel, a mechanically mixed chemical matrix, a glass matrix, a thin film matrix, a rapidly dissolving sample substrate, an etched surface, a patterned surface, a nanostructured surface. These structures, how they are formed, and how they can be implemented for the purpose of liquid surface sampling, according to various embodiments of the invention, are described in the following paragraphs.

Dissolved Chemical Matrix

A chemical matrix is any single chemical that can be dissolved with the analyte in excess ratio between 10× and 20,000× concentration that will co-precipitate as the solvent is evaporated from the solution. The remaining solid is primarily composed of the chemical matrix with the analyte being a minor component of the resulting solid. The chemical matrix can release the analyte back into solution within a time period within a range having a lower limit and/or an upper limit. The range can include or exclude the lower limit and/or the upper limit. The lower limit and/or upper limit can be selected from 0.1, 0.5, 1, 1.5, 2, 2.5, 3, 3.5, 4, 4.5, 5, 5.5, 6, 6.5, 7, 7.5, 8, 8.5, 9, 9.5, 10, 20, 30, 40, 50, 60, 70, 80, 90, 100, 200, 300, 400, 500, 600, 700, 800, 900 and 1000 milliseconds. The lower limit and/or upper limit can be selected from 1, 5, 10, 15, 20, 25, 30, 35, 40, 45, 50, 55 and 60 seconds. The lower limit and/or upper limit can be selected from 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 minutes. For example, according to certain preferred embodiments, the chemical matrix can release the analyte back into solution within a time period of about 15 minutes of the addition of the solvent system used for analysis to the solid. Generally preferred are systems where the dissolution happens on a time frame that is only a fraction of a second, i.e., milliseconds or less. Such rapid time frames allow the analyte to be captured into as small a volume as possible. In other embodiments, slower dissolution can be advantageous or be accommodated using droplet sampling or plug capture sampling mode with the probes. A description of plug capture mode is provided in ElNaggar et al., Liquid Microjunction Surface Sampling Probe Fluid Dynamics: Computation and Experimental Analysis of Coaxial Intercapillary Positioning Effects on Sample Manipulation, J. Am. Soc. Mass spectrum. (2011) 22:1157-1166, which is hereby incorporated by reference in its entirety.

The solid may be at any temperature where the analyte remains chemically unchanged when released back into solution. Physical means of mixing and re-dissolution should not be required, but may be used in conjunction with the chemical matrix.

Biological Matrix

A biological matrix is any mixture of natural materials that can be dissolved with the analyte in excess ratio between 10× and 20,000× concentration that will co-precipitate as the solvent is evaporated from the solution. The remaining solid is primarily composed of the biological matrix with the analyte being a minor component of the resulting solid.

The biological matrix can release the analyte back into solution within a time period within a range having a lower limit and/or an upper limit. The range can include or exclude the lower limit and/or the upper limit. The lower limit and/or upper limit can be selected from 0.1, 0.5, 1, 1.5, 2, 2.5, 3, 3.5, 4, 4.5, 5, 5.5, 6, 6.5, 7, 7.5, 8, 8.5, 9, 9.5, 10, 20, 30, 40, 50, 60, 70, 80, 90, 100, 200, 300, 400, 500, 600, 700, 800, 900 and 1000 milliseconds. The lower limit and/or upper limit can be selected from 1, 5, 10, 15, 20, 25, 30, 35, 40, 45, 50, 55 and 60 seconds. The lower limit and/or upper limit can be selected from 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 minutes. For example, according to certain preferred embodiments, the biological matrix can release the analyte back into solution within a time period of about 15 minutes of the addition of the solvent system used for analysis to the solid.

The solid may be at any temperature where the analyte remains chemically unchanged when released back into solution. Physical means of mixing and re-dissolution should not be required, but may be used in conjunction with the chemical matrix.

Frozen Liquid Matrix

A frozen liquid matrix is any solvent system that dissolves the analyte and creates a solid solution of analyte and solvent in the solid state at temperatures below the freezing point of the solution. The frozen solid must release the analyte back into solution when melted by heating or melting of the solid by addition of warm liquid or gas.

The frozen liquid matrix can release the analyte back into solution within a time period within a range having a lower limit and/or an upper limit. The range can include or exclude the lower limit and/or the upper limit. The lower limit and/or upper limit can be selected from 0.1, 0.5, 1, 1.5, 2, 2.5, 3, 3.5, 4, 4.5, 5, 5.5, 6, 6.5, 7, 7.5, 8, 8.5, 9, 9.5, 10, 20, 30, 40, 50, 60, 70, 80, 90, 100, 200, 300, 400, 500, 600, 700, 800, 900 and 1000 milliseconds. The lower limit and/or upper limit can be selected from 1, 5, 10, 15, 20, 25, 30, 35, 40, 45, 50, 55 and 60 seconds. The lower limit and/or upper limit can be selected from 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 minutes. For example, according to certain preferred embodiments, the frozen liquid matrix can release the analyte back into solution within a time period of about 15 minutes of the addition of the solvent system used for analysis to the solid.

Polymer Matrix

A polymer matrix is any mixture of chemicals containing repeating chemical units in excess of two units. The polymer may be of any physical form and chemical composition. It must polyermerize in such a way as to include the analyte in the polymer as the polymerization reaction takes place.

The polymer matrix must release the analyte in a chemically unchanged form back into solution upon dissolution or disintegration of the polymer matrix to yield analyte dissolved in a liquid. The solid form is primarily composed of the chemical matrix with the analyte being a minor component of the resulting solid.

The polymer matrix can release the analyte back into solution within a time period within a range having a lower limit and/or an upper limit. The range can include or exclude the lower limit and/or the upper limit. The lower limit and/or upper limit can be selected from 0.1, 0.5, 1, 1.5, 2, 2.5, 3, 3.5, 4, 4.5, 5, 5.5, 6, 6.5, 7, 7.5, 8, 8.5, 9, 9.5, 10, 20, 30, 40, 50, 60, 70, 80, 90, 100, 200, 300, 400, 500, 600, 700, 800, 900 and 1000 milliseconds. The lower limit and/or upper limit can be selected from 1, 5, 10, 15, 20, 25, 30, 35, 40, 45, 50, 55 and 60 seconds. The lower limit and/or upper limit can be selected from 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 minutes. For example, according to certain preferred embodiments, the polymer matrix can release the analyte back into solution within a time period of about 15 minutes of the addition of the solvent system used for analysis to the solid.

The solid may be at any temperature where the analyte remains chemically unchanged when released back into solution. Physical means of mixing, dissolution or disintegration should not be required, but may be used in conjunction with the polymer matrix.

Sol Gel/Gel

A gel or sol gel matrix is any chemical or mixture of chemicals that form a gel containing analyte as a minor component of the gel. Gels are a dispersion of molecules of a liquid within a solid in which the solid is the continuous phase and the liquid is the discontinuous phase. The gel must dissolve or otherwise release the analyte from the gel into a free flowing liquid phase solution. This may occur at any temperature where the analyte remains chemically unchanged when released back into solution.

Chemically unchanged means the linear arrangement of atoms that make up the analyte molecule do not change. Covalent bonds remain intact and unchanged. The acid and/or base and/or salt form may be different, but not the primary bonding structure of the analyte molecule.

The gel or sol gel matrix can release the analyte back into solution within a time period within a range having a lower limit and/or an upper limit. The range can include or exclude the lower limit and/or the upper limit. The lower limit and/or upper limit can be selected from 0.1, 0.5, 1, 1.5, 2, 2.5, 3, 3.5, 4, 4.5, 5, 5.5, 6, 6.5, 7, 7.5, 8, 8.5, 9, 9.5, 10, 20, 30, 40, 50, 60, 70, 80, 90, 100, 200, 300, 400, 500, 600, 700, 800, 900 and 1000 milliseconds. The lower limit and/or upper limit can be selected from 1, 5, 10, 15, 20, 25, 30, 35, 40, 45, 50, 55 and 60 seconds. The lower limit and/or upper limit can be selected from 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 minutes. For example, according to certain preferred embodiments, the gel or sol gel matrix can release the analyte back into solution within a time period of about 15 minutes of the addition of the solvent system used for analysis to the solid.

Mechanically Mixed Chemical Matrix

A mechanically mixed chemical matrix is any single chemical or mixture of chemicals in the solid state (undissolved; which includes dispersion, suspensions, melts, and powders) that can be physically mixed with the analyte in excess ratio between 10× and 20,000× concentration that will result in incorporation of the analyte into the large excess of the matrix. The resulting mixed solid is primarily composed of the chemical matrix with the analyte being a minor component of the resulting solid.

The mechanically mixed chemical matrix can release the analyte back into solution within a time period within a range having a lower limit and/or an upper limit. The range can include or exclude the lower limit and/or the upper limit. The lower limit and/or upper limit can be selected from 0.1, 0.5, 1, 1.5, 2, 2.5, 3, 3.5, 4, 4.5, 5, 5.5, 6, 6.5, 7, 7.5, 8, 8.5, 9, 9.5, 10, 20, 30, 40, 50, 60, 70, 80, 90, 100, 200, 300, 400, 500, 600, 700, 800, 900 and 1000 milliseconds. The lower limit and/or upper limit can be selected from 1, 5, 10, 15, 20, 25, 30, 35, 40, 45, 50, 55 and 60 seconds. The lower limit and/or upper limit can be selected from 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 minutes. For example, according to certain preferred embodiments, the mechanically mixed chemical matrix can release the analyte back into solution within a time period of about 15 minutes of the addition of the solvent system used for analysis to the solid.

The solid may be at any temperature where the analyte remains chemically unchanged when released back into solution. Physical means of mixing and re-dissolution should not be required, but may be used in conjunction with the mechanically mixed chemical matrix.

Glass Matrix

A glass is any solid that possesses a non-crystalline, amorphous structure and that exhibits a glass transition when heated towards the liquid state. Glasses can be made of materials such as but not limited to, metallic alloys, ionic melts, aqueous solutions, molecular liquids, and polymers.

The glass matrix can release the analyte back into solution within a time period within a range having a lower limit and/or an upper limit. The range can include or exclude the lower limit and/or the upper limit. The lower limit and/or upper limit can be selected from 0.1, 0.5, 1, 1.5, 2, 2.5, 3, 3.5, 4, 4.5, 5, 5.5, 6, 6.5, 7, 7.5, 8, 8.5, 9, 9.5, 10, 20, 30, 40, 50, 60, 70, 80, 90, 100, 200, 300, 400, 500, 600, 700, 800, 900 and 1000 milliseconds. The lower limit and/or upper limit can be selected from 1, 5, 10, 15, 20, 25, 30, 35, 40, 45, 50, 55 and 60 seconds. The lower limit and/or upper limit can be selected from 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 minutes. For example, according to certain preferred embodiments, the glass matrix can release the analyte back into solution within a time period of about 15 minutes of the addition of the solvent system used for analysis to the solid.

Thin Film Matrix

A thin film is a layer of material ranging from fractions of a nanometer to several micrometers in thickness. For example a thin film can have a thickness within a range having a lower limit and/or an upper limit. The range can include or exclude the lower limit and/or the upper limit. The lower limit and/or upper limit can be selected from 0.1, 1, 10, 100, 1,000, 10,000, 100,000, 1,000,000, and 10,000,000 nm. For example, according to certain preferred embodiments, the analyte can have a thickness of less than 1 mm.

A thin film matrix maybe deposited with the analyte or in a separate step before analyte solution application. If the thin film is the matrix, the dried matrix will re-dissolve in the analyte solution and precipitate as a solid mixture of film material and analyte.

The thin film matrix can release the analyte back into solution within a time period within a range having a lower limit and/or an upper limit. The range can include or exclude the lower limit and/or the upper limit. The lower limit and/or upper limit can be selected from 0.1, 0.5, 1, 1.5, 2, 2.5, 3, 3.5, 4, 4.5, 5, 5.5, 6, 6.5, 7, 7.5, 8, 8.5, 9, 9.5, 10, 20, 30, 40, 50, 60, 70, 80, 90, 100, 200, 300, 400, 500, 600, 700, 800, 900 and 1000 milliseconds. The lower limit and/or upper limit can be selected from 1, 5, 10, 15, 20, 25, 30, 35, 40, 45, 50, 55 and 60 seconds. The lower limit and/or upper limit can be selected from 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 minutes. For example, according to certain preferred embodiments, the thin film matrix can release the analyte back into solution within a time period of about 15 minutes of the addition of the solvent system used for analysis to the solid.

Rapidly Dissolving Sample Substrate

A solid material can be used that is formed into sheets that will not dissolve in sample solution, but will dissolve in another solvent system or in a similar solvent with pH greater than or less than the sample solution pH by at least two pH units. The substrate may be a dissolving surface on a non-dissolving support or it may be a dissolving support.

The rapidly dissolving sample substrate can release the analyte back into solution within a time period within a range having a lower limit and/or an upper limit. The range can include or exclude the lower limit and/or the upper limit. The lower limit and/or upper limit can be selected from 0.1, 0.5, 1, 1.5, 2, 2.5, 3, 3.5, 4, 4.5, 5, 5.5, 6, 6.5, 7, 7.5, 8, 8.5, 9, 9.5, 10, 20, 30, 40, 50, 60, 70, 80, 90, 100, 200, 300, 400, 500, 600, 700, 800, 900 and 1000 milliseconds. The lower limit and/or upper limit can be selected from 1, 5, 10, 15, 20, 25, 30, 35, 40, 45, 50, 55 and 60 seconds. The lower limit and/or upper limit can be selected from 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 minutes. For example, according to certain preferred embodiments, the rapidly dissolving sample substrate can release the analyte back into solution within a time period of about 15 minutes of the addition of the solvent system used for analysis to the solid.

Etched Surface

Etched surfaces can be employed. Etched surfaces can have various combinations of surface area and pore size. An etched surface can have a surface area within a range having a lower limit and/or an upper limit. The range can include or exclude the lower limit and/or the upper limit. The lower limit and/or upper limit can be selected from 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900 and 3000 m2/g. For example, according to certain preferred embodiments, an etched surface can have a surface area in a range of from 300 to 2,000 m2/g.

An etched surface can have an average pore size within a range having a lower limit and/or an upper limit. The range can include or exclude the lower limit and/or the upper limit. The lower limit and/or upper limit can be selected from 10, 20, 30, 40, 50, 60, 70, 80, 90, 100, 200, 300, 400, 500, 600, 700, 800, 900 and 1000 Å. For example, according to certain preferred embodiments, an etched surface can have an average pore size of greater than 20 Å.

Etched surfaces typically have the surface layer or portions of the substrate removed to create high surface area and pore sizes greater than 20 Å. To use an etched surface as a means of molecular dispersion, the liquid sample is dispensed on to the etched substrate and evaporation of an amount of the sample results in a solid sample on the etched surface. The amount of the sample that evaporates can be within a range having a lower limit and/or an upper limit. The range can include or exclude the lower limit and/or the upper limit. The lower limit and/or upper limit can be selected from 75, 80, 85, 90, 91, 92, 93, 94, 95, 96, 97, 98, 99 and 100%. For example, according to certain preferred embodiments, the amount of the sample that evaporates can be greater than 90%.

The analyte can re-dissolve into liquid within a time period within a range having a lower limit and/or an upper limit. The range can include or exclude the lower limit and/or the upper limit. The lower limit and/or upper limit can be selected from 0.1, 0.5, 1, 1.5, 2, 2.5, 3, 3.5, 4, 4.5, 5, 5.5, 6, 6.5, 7, 7.5, 8, 8.5, 9, 9.5, 10, 20, 30, 40, 50, 60, 70, 80, 90, 100, 200, 300, 400, 500, 600, 700, 800, 900 and 1000 milliseconds. The lower limit and/or upper limit can be selected from 1, 5, 10, 15, 20, 25, 30, 35, 40, 45, 50, 55 and 60 seconds. The lower limit and/or upper limit can be selected from 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 minutes. For example, according to certain preferred embodiments, the analyte can re-dissolve into liquid within a time period of about 15 minutes of the application of the liquid to the sample containing surface.

Patterned Surface

Patterned surfaces are surfaces onto which a regular array of mechanical structures has been created. The structures must result in high surface area and contain pores either within the substrate material or the structures themselves.

The structures can have an average pore size within a range having a lower limit and/or an upper limit. The range can include or exclude the lower limit and/or the upper limit. The lower limit and/or upper limit can be selected from 10, 20, 30, 40, 50, 60, 70, 80, 90, 100, 200, 300, 400, 500, 600, 700, 800, 900 and 1000 Å. For example, according to certain preferred embodiments, the structures can have an average pore size of greater than 20 Å.

The structures can have an average pore size within a range having a lower limit and/or an upper limit. The range can include or exclude the lower limit and/or the upper limit. The lower limit and/or upper limit can be selected from 10, 20, 30, 40, 50, 60, 70, 80, 90, 100, 200, 300, 400, 500, 600, 700, 800, 900 and 1000 Å. For example, according to certain preferred embodiments, the structures can have an average pore size of greater than 20 Å.

The substrate and structures need not be made from the same material. The structures may be molded, deposited, etched, bonded, ablated or machined. The structures themselves and/or the pattern of structures must have the ability to enhance the dissolution of solid material so that material dried on the surface from solution, deposited from vapor, or applied in a solid form will re-dissolve within a time period measured from application of liquid to the surface. The time period can be within a range having a lower limit and/or an upper limit. The range can include or exclude the lower limit and/or the upper limit. The lower limit and/or upper limit can be selected from 0.1, 0.5, 1, 1.5, 2, 2.5, 3, 3.5, 4, 4.5, 5, 5.5, 6, 6.5, 7, 7.5, 8, 8.5, 9, 9.5, 10, 20, 30, 40, 50, 60, 70, 80, 90, 100, 200, 300, 400, 500, 600, 700, 800, 900 and 1000 milliseconds. The lower limit and/or upper limit can be selected from 1, 5, 10, 15, 20, 25, 30, 35, 40, 45, 50, 55 and 60 seconds. The lower limit and/or upper limit can be selected from 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 minutes. For example, according to certain preferred embodiments, the time period can be about 15 minutes.

Nanostructured Surface

A nanostructured surface can have nano-scale physical structures naturally occurring, created and/or arranged on the surface. The nano-scale physical structures can have at least one dimension (length, height, and/or width) within a range having a lower limit and/or an upper limit. The range can include or exclude the lower limit and/or the upper limit. The lower limit and/or upper limit can be selected from 0.05, 0.1, 1, 5, 10, 15, 20, 25, 30, 35, 40, 45, 50, 55, 60, 65, 70, 75, 80, 85, 90, 95, 100, 105, 110, 115, 120, 125, 130, 135, 140, 145 and 150 nanometers. For example, according to certain preferred embodiments, the nano-scale physical structures can have at least one dimension (length, height, and/or width) within a range of 0.1 to 100 nanometers.

The structures may be molded, deposited, etched, bonded, ablated, and/or machined. The structures themselves and/or the pattern of structures must have the ability to enhance the dissolution of solid material so that material dried on the surface from solution, deposited from vapor, or applied in a solid form will re-dissolve a time period measured from application of liquid to the surface. The time period can be within a range having a lower limit and/or an upper limit. The range can include or exclude the lower limit and/or the upper limit. The lower limit and/or upper limit can be selected from 0.1, 0.5, 1, 1.5, 2, 2.5, 3, 3.5, 4, 4.5, 5, 5.5, 6, 6.5, 7, 7.5, 8, 8.5, 9, 9.5, 10, 20, 30, 40, 50, 60, 70, 80, 90, 100, 200, 300, 400, 500, 600, 700, 800, 900 and 1000 milliseconds. The lower limit and/or upper limit can be selected from 1, 5, 10, 15, 20, 25, 30, 35, 40, 45, 50, 55 and 60 seconds. The lower limit and/or upper limit can be selected from 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 minutes. For example, according to certain preferred embodiments, the time period can be about 15 minutes.

Example 1

Figure 1B:
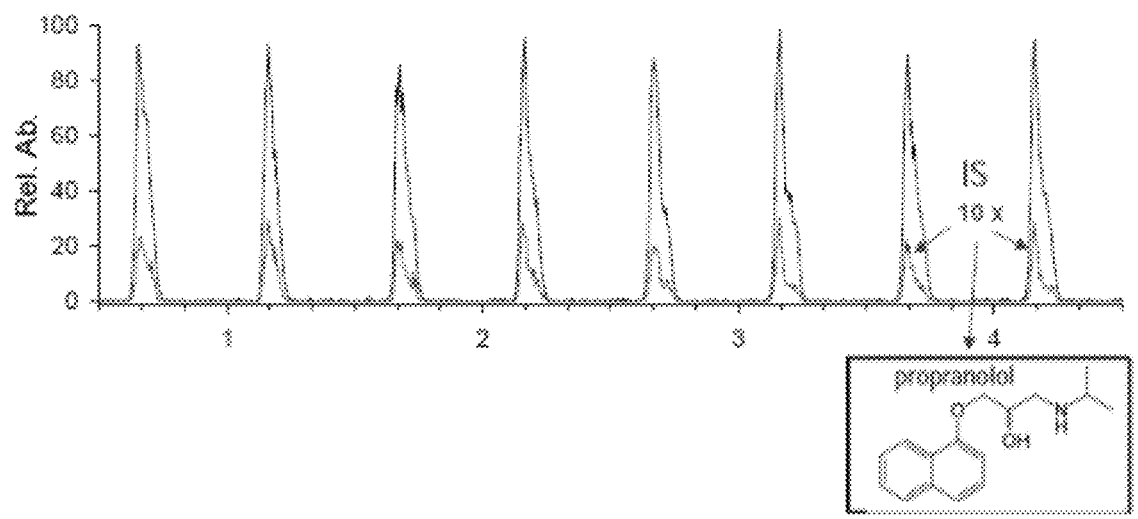
FIG. 1B shows only the data obtained from the analysis of the 500 ng/mL verapamil spots to illustrate the basic peak shape, reproducibility, and sample-to-sample analysis time obtained with this method.

The Selected Reaction Monitoring (SRM) ion current chronograms in FIG. 1A were obtained from the sampling of 64 different spots (1 µL deposited) of the analyte verapamil (500-2.5 ng/mL, 8 replicates for each concentration) and propranolol internal standard (100 ng/mL) from a stainless steel MALDI plate insert. These sample spots all contained 1.5 µg of MALDI matrix (1 µL×1.5 mg/mL α-cyano-4-hydroxy cinnamic acid). The eluting solvent was 80/20 (v/v) ACN/water (0.1% formic acid) at 10 µL/min. FIG. 1B shows only the data obtained from the analysis of the 500 ng/mL verapamil spots 101 to illustrate the basic peak shape, reproducibility, and sample-to-sample analysis time obtained with this method. In this particular example, and the other experiments shown here, the total sample-to-sample analysis time was 30 s. Of this total time, only about 3-3.5 s were spent in the actual formation of the sampling liquid microjunction and aspiration of the liquid back into the probe from the sampling point. The rest of the time was included in the analysis to ensure that the sample was completely flushed from the probe prior to the next spot analysis to minimize sample carryover.

While the invention has been described in terms of specific embodiments, it is evident in view of the foregoing description that numerous alternatives, modifications and variations will be apparent to those skilled in the art. Accordingly, the invention is intended to encompass all such alternatives, modifications and variations which fall within the scope and spirit of the invention and the following claims. Therefore, the spirit and scope of the appended claims should not be limited to the description of the preferred versions contained herein.

The reader's attention is directed to all papers and documents which are filed concurrently with this specification and which are open to public inspection with this specification, and the contents of all such papers and documents are incorporated herein by reference.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means for" performing a specified function, or "step for" performing a specific function, is not to be interpreted as a "means" or "step" clause as specified in 35 U.S.C §112, sixth paragraph. In particular, the use of "step of" in the claims herein is not intended to invoke the provisions of 35 U.S.C §112, sixth paragraph.

We claim:

1. A method for performing surface sampling of a sample containing an analyte, comprising the steps of:

combining the analyte with a matrix material in a solvent for the analyte and for the matrix material to produce an analyte-matrix material solution where the matrix material is at least in a molar excess 10 times greater than the analyte;

placing the analyte-matrix material solution on a support;

removing the solvent to solidify the analyte and matrix material on the support, such that analyte-analyte interactions are prevented and the analyte can be re-solubilized for further analysis; and, surface sampling the solidified analyte and matrix material, comprising the step of flowing solvent onto the solidified analyte and matrix material with a surface sampling probe and removing the analyte-matrix material solution with the surface sampling probe.

2. The method of claim 1, wherein a liquid microjunction is formed between the surface sampling probe and the sample.

3. The method of claim 1, further comprising the step of analyzing the analyte-containing solvent.

4. The method of claim 3, wherein the analyzing step comprises electrospray mass spectrometry.

5. The method of claim 1, wherein the matrix material in molar excess to the analyte has a structure, and wherein the structure is a dissolved chemical matrix.

6. The method of claim 1, wherein the matrix material in molar excess to the analyte has a structure, and wherein the structure is a biological matrix.

7. The method of claim 1 further comprising placing the analyte on a stage with the matrix material.

* * * * *